United States Patent [19]

Brodsky et al.

[11] 4,137,226
[45] Jan. 30, 1979

[54] 3,3-(1,1'-BIPHENYL-2,2'-DIYL)-1-(4-METHYLPHENYL)-1-TRIAZENE

[75] Inventors: Lee D. Brodsky, Parsippany; Mark L. Moskowitz, Wayne, both of N.J.; Ralph G. D. Moore, Chenango Forks, N.Y.

[73] Assignee: GAF Corporation, New York, N.Y.

[21] Appl. No.: 861,669

[22] Filed: Dec. 19, 1977

[51] Int. Cl.$^2$ ............................................. C07C 107/04
[52] U.S. Cl. ................................. 260/140; 204/159.11
[58] Field of Search ................................. 260/140, 164

[56] References Cited

U.S. PATENT DOCUMENTS 2,136,456  11/1938  Moran et al. ..................... 260/140 X Primary Examiner—Charles F. Warren
Attorney, Agent, or Firm—Walter C. Kehm; Edward G. Comrie

[57] ABSTRACT

A novel triazene compound which upon thermal or photochemical decomposition provides free radicals for polymer initiation and methods using same.

1 Claim, No Drawings

3,3-(1,1'-BIPHENYL-2,2'-DIYL)-1-(4-METHYLPHENYL)-1-TRIAZENE

BACKGROUND OF THE INVENTION

The initiation of polymerization by the use of compounds which can be broken down into free radicals is well known in the polymer art. The triazene of the present invention is 3,3-(1,1'-biphenyl-2,2'-diyl)-1-(4-methylphenyl)-1-triazene, the formula of which is:

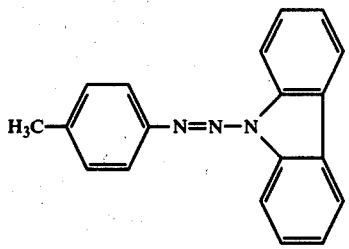

The advantage of the present compound is believed to be that upon decomposition of this particular triazene two free radicals are formed. The free radicals formed add to monomers produce another radical. Such radical regeneration is characteristic of chain reactions. The radicals formed in the initiation step may then add additional monomer molecules resulting in chain growth or propagation. The chain would continue to grow if it were not terminated in some way which often takes place by a combination or coupling of the growing radical chains.

The general sequence of polymerization by a free radical mechanism is initiation in which the free radical precursor decomposes to form one or more free radicals. The free radicals then attach themselves to the monomers. In a series of steps called propagation the monomers activated by free radicals can attach themselves to other monomers. The propagation may proceed by several monomer radicals continuing to attach themselves one to the other until at some point the sequence is terminated by the completion of a chain without a recurrence of a free radical attachment or active site. This usually occurs by the combination or coupling of the growing radical chains.

The kinetic chain length is directly proportional to monomer concentration squared and inversely proportional to the radical concentration or polymerization rate. An increase in polymerization rate or radical concentration will produce smaller polymer molecules. The kinetic chain length is more a characteristic of a particular monomer and does not depend completely on the method of initiation.

DETAILED DESCRIPTION OF THE INVENTION

Preparation of 3,3-(1,1'-biphenyl-2,2'-diyl)-1-(4-methylphenyl)-1-triazene.

EXAMPLE 1

A stirred partial solution of 16.7g (0.1 mole) carbazole in 100 ml dimethylformamide was reacted with 4.8g (0.1 mole) 50% sodium hydride dispersed in oil. A slow evolution of gas was observed. An excess sodium hydride was added. The mixture was stirred until all the carbazole was dissolved and little or no gas came off. The excess sodium hydride was filtered off and the solution was treated with 20.6g (0.1 mole) of 4-methylbenzenediazonium fluoborate. The methylbenzenediazonium fluoborate dissolved exothermally. A precipitate formed. The precipitate slurry was refrigerated overnight. The crude triazene was filtered, rinsed with dimethylformamide, then water, and vacuum dried at 45° C. and 30 inches Hg to constant weight. The yield was 11.2g (39.2%), m. 139°–41°. From the mother liquor 6.6g of material melting over 210°, presumably unreacted carbazole was recovered. The crude triazene was recrystallized from ethanol-acetone and activated carbon to give 8.2g (28.7%) purified material, m. 147°–8° (dec.), N found 14.63, 14.67, 14.69, 14.77 (calc. 14.73%).

Triazenes are recognized as being readily affected by actinic radiation. It was further supposed that upon activation with an actinic source of radiation the compound of the present invention would probably cleave at the triazo portion of the molecule and produce a diazo free radical and a carbazole free radical. Several other triazene compounds having cyclic and heterocyclic moieties were prepared, but none possessed the activity of the compound of the present invention.

The polymerization initiator triazene of the present invention was compared with the generally accepted commercial free radical polymerization initiator azobisisobutyronitrile which is sold under the name VAZO 64 ®, a product of the Dupont Company. The amount of polymerization initiator required is determined empirically. The greater the amount of initiator the shorter will be the chain length.

Methylmethacrylate containing 10 ppm methylethylhydroquinone was passed through a column of absorption grade $Al_2O_3$ of 80–200 mesh to remove the inhibitor prior to charging the monomer to polymerization tubes. 20 Grams of methylmethacrylate monomer and 0.100g azobisisobutyronitrile was charged to polymerization tube A. The azobisisobutyronitrile was present in an amount of 0.5% wt/wt or 0.00061 moles. A second polymerization tube also containing 20 grams of methylmethacrylate had added to it 0.174g of the triazene of the present invention which also is present in an amount of 0.00061 mole. The polymerization tubes were then frozen using a dry ice - acetone bath and evacuated to 5 mm of mercury. They were then purged with nitrogen to remove any oxygen which might be present and allowed to thaw. This procedure was repeated five times after which the tubes were evacuated and sealed. The polymerization tubes and contents were allowed to reach room temperature. They were then placed in a constant temperature bath at 65°, plus or minus one degree C. for 21 hours. The polymerization tubes were cooled, the seal broken and the contents rinsed from the tubes using a total of 250 ml of benzene for each tube. The polymer was dissolved with gentle agitation at room temperature. Each solution of polymer in benzene was then stirred into three liters of methanol. This precipitated the polymers which were then washed three times with methanol. The polymer solids were dried to constant weight at 45° C. in a high vacuum. The yield for the commercial polymer initiator batch was 91.6% and the yield of the batch using the triazene of the present invention yielded 91.1%.

After precipitation and washing, the polymer of the commercial initiator was pure white and the polymer produced using the triazene of the present invention was off-white.

The relative viscosities of 1% wt by volume solution in dioxane of the two products was measured. The product of the commercial polymer initiator gave a viscosity of 2.47 while that of the triazene of the present invention gave a viscosity of 5.41.

No cross linking was observed in either benzene or dioxane. Workers skilled in the art are aware that cross linking is evidenced by failure to dissolve completely or mere swelling of the polymer of methylmethacrylate should cross linking have occurred. The viscosity is a measure of the chain length obtained in the polymerization and it clearly indicates the greater chain length produced by the triazene of the present invention.

A second series of polymerization were carried out in similar manner to the above except that the methylmethacrylate monomer was dissolved on a 50% wt/wt basis using benzene as a solvent. The results in this instance were not comparable to the polymerization carried out using methylmethacrylate undiluted.

The triazene of the present invention 3,3-(1,1'-biphenyl-2,2'-diyl)-1-(4-methylphenyl)-1-triazene has been shown to be an effective free radical polymerization initiator with methylmethacrylate monomer. It will be apparent to those skilled in the art that an effective free radical source can be used in many other types of polymerization or situations wherein a source of free radicals may be useful.

What is claimed is:

1. The compound of 3,3-(1,1'-biphenyl-2,2'-diyl)-1-(4-methylphenyl)-1-triazene,

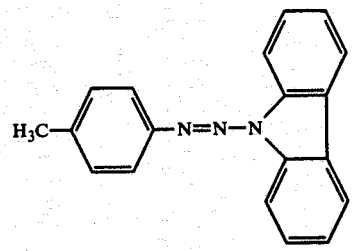

* * * * *